(12) United States Patent
Mann et al.

(10) Patent No.: US 6,199,554 B1
(45) Date of Patent: Mar. 13, 2001

(54) METHOD AND APPARATUS FOR COMBINING INJURY-MEDIATED THERAPY AND DRUG DELIVERY

(75) Inventors: Michael J. Mann, Newton, MA (US); Umer Sayeed-Shah, Wappingers Falls, NY (US); Victor Dzau, Newton, MA (US); Lawrence H. Cohn, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/049,882

(22) Filed: Mar. 27, 1998

(51) Int. Cl.$^7$ ................................................. A61B 19/00
(52) U.S. Cl. .................... 128/898; 604/20; 604/890.1; 604/48; 606/2; 607/89
(58) Field of Search ................ 128/898; 604/20, 604/890.1, 46, 48, 49; 606/15, 7, 2; 607/88, 89

(56) References Cited

U.S. PATENT DOCUMENTS

| | | | |
|---|---|---|---|
| 4,658,817 | * 4/1987 | Hardy | 128/303.1 |
| 5,109,859 | 5/1992 | Jenkins | 128/662.03 |
| 5,628,761 | 5/1997 | Rizik | 606/170 |
| 5,672,170 | 9/1997 | Cho et al. | 606/12 |
| 5,683,366 | 11/1997 | Eggers et al. | 604/114 |
| 5,766,164 | * 6/1998 | Mueller et al. | 606/15 |
| 5,846,225 | 12/1998 | Rosengart et al. | 604/115 |
| 5,846,720 | * 12/1998 | Foulkes et al. | 435/6 |
| 5,900,433 | * 5/1999 | Igo et al. | 514/530 |
| 5,913,853 | * 6/1999 | Loeb et al. | 606/15 |
| 5,925,012 | * 7/1999 | Murphy-Chutorian et al. | 604/30 |

OTHER PUBLICATIONS

Bosman et al., "Ultrastructural Alterations in Heated Canine Myocardium", Lasers in Surgery and Medicine 17:39–48 (1995).

Fleischer et al., "One–Month Histologic Response of Transmyocardial Laser Channels With Molecular Intervention", Ann. Thorac. Surg. 62:1051–1058 (1996).

Hussain et al., "A Review of the Literature: Transmyocardial Laser Revascularization", Journal of Clinical Laser Medicine & Surgery 15:57–63 (1997).

Leung et al., "Vascular Endothelial Growth Factor Is a Secreted Angiogenic Mitogen", Science 246:1306–1309 (1989).

Lin et al., "Expression of Recombinant Genes in Myocardium in Vivo After Direct Injection of DNA", Circulation 82:2217–2221 (1990).

Mirhoseini et al., "Clinical Report: Laser Myocardial Revascularization", Lasers in Surgery and Medicine 6:459–461 (1986).

* cited by examiner

Primary Examiner—Dinh X. Nguyen
(74) Attorney, Agent, or Firm—Clark & Elbing LLP

(57) ABSTRACT

A method of enhancing injury-induced revascularization of a tissue as treatment of a disease, such as coronary artery disease, is described. The method involves (i) creating injury in a tissue (e.g., muscle, such as cardiac muscle) by, for example, use of a laser, an ultrasonic device, or a Thermal probe, and (ii) injecting into the tissue a revascularization-promoting molecule or a nucleic acid molecule encoding a revascularization-promoting molecules Also described is an apparatus that can be used to practice this method.

28 Claims, 3 Drawing Sheets

METHOD AND APPARATUS FOR COMBINING INJURY-MEDIATED THERAPY AND DRUG DELIVERY

BACKGROUND OF THE INVENTION

This invention relates to a coordination of injury-inducing revascularization treatment and drug delivery to improve vascularization and increase gene expression.

The morbidity and mortality of ischemic heart disease are directly attributable to myocardial injury as a result of limited blood flow from atherosclerotic narrowing of the epicardial coronary arteries. Transmyocardial revasculaization (TMR) reduces the symptoms and morbidity of patients with end-stage ischemic heart disease (Fleischer et al., Ann. Thorac. Surg. 62: 1051–1058, 1996) IMP involves the use of a high-powered carbon dioxide ($CO_2$) laser to create transmyocardial channels in regions of critically ischemic tissue. It has been speculated that these channels act as conduits to shunt oxygenated blood from the left ventricle into the extensive intramyocardial vascular plexus. However, an alternative mechanism proposed attributes the healing response to laser injury accompanied by neovascularization and increased collateral perfusion of thermally damaged tissue (Fleischer, supra).

SUMMARY OF THE INVENTION

The invention provides a method of enhancing injury-induced revascularization of a tissue as treatment of a disease, such as coronary artery disease. The method involves (i) creating injury in a tissue, e.g., as a result of mechanical, chemical, electromagnetic, or thermal perturbation, by making a channel in the tissue (e.g., muscle, such as cardiac muscle) by use of, e.g., a laser (a carbon dioxide, holmium:yttrium-aluminum garnet (HO:YAG), or thulium-holmium-chromium (THC-YAG) laser), an ultrasonic device, or a thermal probe, and (ii) injecting into the tissue a revascularization-promoting molecule (e.g., a protein, such as a pro-angiogenic factor, for example, vascular endothelial growth factor, fibroblast growth factor, platelet derived growth factor, insulin-like growth factor, epidermal growth factor, transforming growth factor, hepatocyte growth factor, proliferin, angiotropin, or angiopoietin) or a nucleic acid molecule (e.g., naked DNA) encoding a revascularization-promoting molecule.

Preferably, the track of the injection carried out using the method of the invention parallels the channel, and preferably the injection track is more than 1 mm and less than 4 mm from the channel. Also, the time between creating the channel and making the injection in the method preferably is less than 5.0 seconds, for example, less than 1.0 second, or less than 0.1 second. The number of the injections preferably is equal or greater than the number of the channels in the treated tissue.

Use of the method of the invention results in improvement of a condition of the disease to a greater degree than results from injury-induced revascularization treatment alone. For example, the condition can improve as a result of increased vascularization of tissue (e.g., muscle or connective tissue) affected by the disease (e.g., peripheral vascular disease or wound healing).

One example of a symptom that can be ameliorated using the method of the invention is abnormal left ventricular wall motion or abnormal myocardial function. Myocardial function can be assessed by measurements such as end-systolic elastance, the ratio of end systolic elastance, the volume of a (theoretically) completely unloaded ventricle, preload recruitable stroke work, comparison of ejection fraction and end diastolic volume, or the derivative of pressure divided by the derivative of time.

The cellular entry of a nucleic acid molecule administered to a tissue using the method of the invention can be facilitated by non-live viral mediated transfer. The nucleic acid molecule can be mixed with a lipid polyamine admixture. Also, the nucleic acid molecule can be operably linked to a promoter in a recombinant viral vector, such as a retrovirus, adeno-virus, adeno-associated virus, or lentivirus vector. A molecule administered using the method of the invention can undergo sustained release, e.g., as a result of encompassing the molecule within a polymeric microsphere, or linking the molecule to a complex, biodegradable molecule.

The invention also includes a method of increasing gene expression in a tissue. This method involves (i) creating tissue injury, e.g., as a result of mechanical, chemical, electromagnetic, or thermal perturbation, by making a channel in the tissue, e.g., by laser (a carbon dioxide, holmium:yttrium-aluminum garnet (HO:YAG), or thulium-holmium-chromium (THC-YAG) laser), ultrasonic, or thermal perturbation, and (ii) injecting into the tissue a nucleic acid molecule (e.g., naked DNA) containing the gene. This method results in increased expression of the gene compared to expression that results from injection of the nucleic acid molecule alone. Preferably, the track of the injection parallels the channel.

Cellular entry of a nucleic acid molecule using the method of the invention can be facilitated by non-live viral mediated transfer. A nucleic acid molecule can be mixed with a lipid polyamine admixture prior to administration. The nucleic acid molecule can be operably linked to a promoter in a recombinant viral vector, such as a retrovirus, adenovirus, adeno-associated virus, or lentivirus vector.

Also included in the invention is an apparatus for enhancing injury-induced revascularization of a tissue as a treatment of a disease. This apparatus includes, in operable linkage, a means for creating a channel in the tissue, and a means for injecting a biologically active compound into the tissue. The means for creating the channel in the tissue can include a source of directable heat, such as an aperture for a laser (e.g., a carbon dioxide laser gun) or an ultrasound probe, or a thermal probe.

The means for injecting the molecule into the tissue can include a cannula (e.g., a needle) in fluid communication with a fluid chamber (e.g., a syringe or a piece of tubing), and a fluid ejection means (e.g., a plunger or a pump). The cannula and the source of directable heat can be positioned in the apparatus so that the cannula and the pathway of the directable heat are parallel to one another, preferably about 1 mm to 4 mm apart.

In one embodiment of the apparatus of the invention, the aperture and one end of the cannula are positioned adjacent to one another when the apparatus is in a resting position. This apparatus also includes a projection means for projecting the cannula into the tissue, moving the apparatus into an active position, and for removing the cannula from the tissue, moving the apparatus into the resting position, when the aperture and the one end of the cannula are positioned near the surface of the tissue.

By "parallel" is meant that, for any given depth of the tissue, the distance between center line of the channel and the center line of the injection track left by the injecting needle, is constant to within 0.5 mm.

By "tissue injury" is meant cell damage that results from chemical, mechanical, electromagnetic or thermal perturbations.

By "pro-angiogenic" is meant stimulating growth of new blood vessels, with of either microvessels of less than 100 $\mu$M in diameter or larger and more muscular vessels.

By "revascularization-promoting" is meant stimulating the appearance of endothelial cells in the area of tissue injury.

One advantage of the present invention is the actual improvement of symptoms by increasing tissue vascularization This advantage is attributed to the careful placement of the protein or DNA injectate at a standard distance and parallel orientation with respect to the channel site. As a result of this careful placement, gene expression of the injected DNA is maximized, and the effect of the injected or expressed protein is also maximized in the area of tissue injury. In one preferred embodiment of the invention, the simultaneous delivery of the injectate and the formation of the channel facilitates the required placement precision, especially in actively contracting tissue such as a beating heart. As an additional advantage, the expression of any protein in a tissue can be enhanced by co-treatment with carefully placed tissue injury.

The invention also provides the advantage of providing for possibly more global factor/DNA delivery combined with local TMR treatment, and, in this context, allows for a disparity in timing between TMR and drug or nucleic acid delivery. Another distinguishing advantage of the invention is the combination of TMR with drug or nucleic acid delivery through minimally invasive or non-invasive means.

Other features and advantages of the invention will be apparent from the following detailed description thereof, and from the claims.

DETAILED DESCRIPTION OF THE INVENTION

Figure 1:
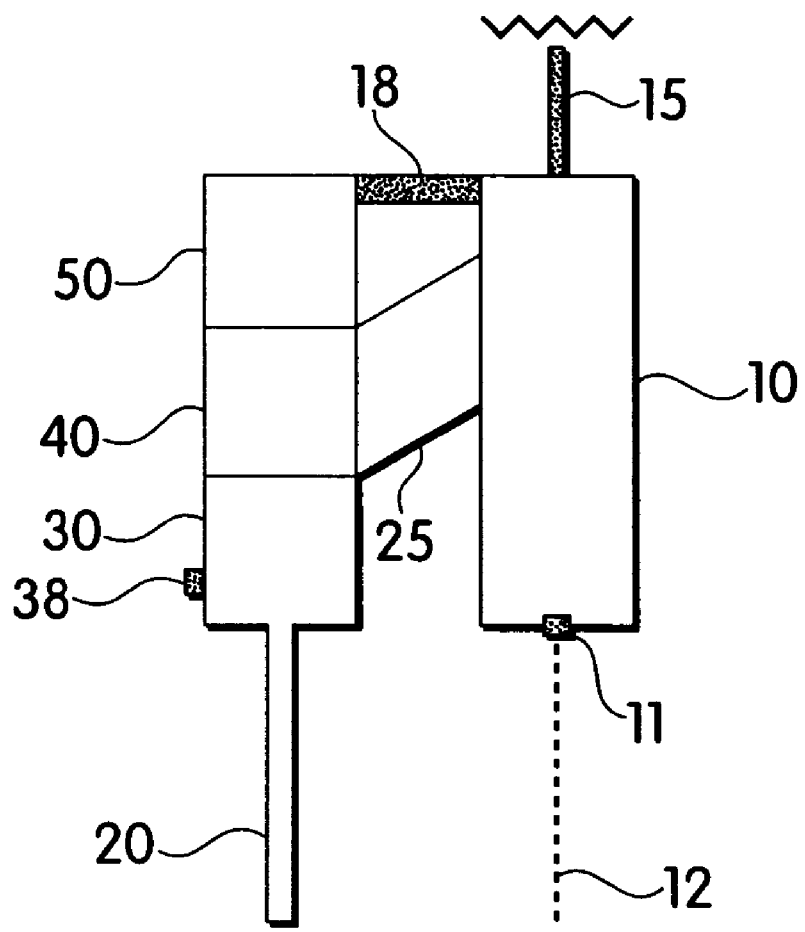
FIG. 1 is a schematic representation of an embodiment of the apparatus of the invention.

In general, the invention relates to a method of enhancing revascularization by inducing injury in a tissue in conjunction with drug delivery (protein or DNA injection) such that the interaction between the two treatments results in greater revascularization than observed with either treatment alone. To achieve this effect, the method emphasizes that the relationship between channel formation and protein or DNA delivery must be carefully regulated in terms of distance between channel and injection sites as well as the orientation of the channel and the injection track though the tissue.
Optimization of injury-mediated enhancement of transgene expression.

Transgene expression of a plasmid with the reporter gene $\beta$-galactosidase was evaluated to determine the effects of transmyocardial thermal injury and the distance to the injury site. A model of transmyocardial thermal injury was used to mimic the photothermal effects of water-dominated tissue vaporization processes characteristic of infrared, or non-ultraviolet, wavelength lasers. A 0.8 mm thermal probe at 1600° F. was used to induce the thermal injury. Subepicardial injections of a pSV $\beta$-galactosidase plasmid (100 $\mu$g) in 100 $\mu$g ddH$_2$O were administered at 1.5 mm, 3.0 mm, and at less than 0.5 mm from the site of thermal injury.

The results demonstrated that myocardial transgene expression is enhanced by transmyocardial thermal injury when DNA injections occurred at 1.5 and 3.0 mm from the thermal injury site, but not at less than 0.5 mm. For example, $\beta$-galactosidase expression with thermal injury at less than 0.5 mm was 248±50 pg/mg compared to 250±38 pg/mg tissue extract. In contrast, $\beta$-galactosidase expression levels with thermal injury at 1.5 and 3.0 mm from the thermal injury site was 391±33 and 299±37 pg/mg tissue extract, respectively.

Previous attempts at viral-mediated gene transfer under conditions of transmyocardial laser revascularization (TMR) have been associated with a significant inflammatory response, but no evidence of enhanced transgene expression (Fleisher et al., Ann. Thorac. Surg. 62: 1051–1058, 1996). In contrast, the present results demonstrate that transmyocardial thermal injury, which is analogous to TMR, does increase gene expression. Under the above described experimental conditions, using "naked" plasmid DNA and thermal injury, the ideal site for injection is between 1 and 4 mm from the injury This discovery indicates that coadministration of tissue injury (e.g. channel formation via TMR or transmyocardial thermal injury, chemical, mechanical or electromagnetic injury) with DNA injection can be used as a method of increasing transgene expression in the tissue of choice.

VEGF effects on TMR-induced revascularization and cardiac function.

Given that the expression of pro-angiogenic factors can enhance TMR-induced revascularization, the above transgene expression techniques were used to investigate the effects of vascular endothelial growth factor (VEGF) on TMR-induced revascularization and cardiac function.
Methods Left mini-thoracotomy. Yorkshire pigs were premedicated with ketamine (10 mg/kg), intubated and maintained with general inhalational anesthesia with 2% isoflorane. Cefazolin (40 mg/kg), Mg SO$_4$ (40 mg/kg), and bretylium tosylate (10 mg/kg) were given intravenously as prophysaxis against would infection and atrial and ventricular dysrytlumias. A left anterior mini-thoracotomy was performed through the fourth interspace and the pericardium incised and suspended to reveal the free wall of the left ventricle.

Gene delivery in non-ischemic myocardium. Three equidistant 100 $\mu$l intramyocardial injections were placed with a 25-gauge needle within 4 mm of TMR sites. Two vehicles, either fusigenic HVJ-liposomes or naked plasmid were used to deliver an expression plasmid (pSV) containing the gene encoding $\beta$-galactosidase ($\beta$-gal) with an SV40 promoter and enhancer. This promotor has been determined to be similarly effective in driving transgene expression in both ischemic and non-ischemnic myocardium Win et al., Circ. 82: 2217–2221, 1990). Two doses of DNA each were used for myocardial transfection; 5 and 15 $\mu$g for HVJ-liposomes and 100 and 200 $\mu$g for naked plasmid. Similar injections were placed around 22-gauge needle puncture sites on non-TMR myocardium. The protocol utilized for HVJ-liposome preparation has been well described (Daneda et al., Science 243:335–338, 1989). A PGL2 expression plasmid, using an SV40 early promoter and enhancer, but encoding the gene for firefly luciferase was injected at TMR sites in an identical manner to be used as a control.

Animal were allowed to recover, and were sacrificed at three days post-transduction. The heart was cold-crystalloidarrested, and then removed from the mediastinum. Two individual, 10 mm length, full thickness myocardial samples were taken at 5 mm intervals from each TMR and infection site, and snap frozen in liquid nitrogen. 60 samples from TMR-transfected myocardium and 20 samples from non-TMR transfected myocardium in addition to 20 control samples of TMR-luciferase transfected myocardium were taken for analysis.

Chronically ischemic hearts. Forty Yorkshire pigs were divided into six groups. They underwent placement of an ameroid constrictor around the proximal left circumflex artery via a left mini-thoracotomy, and were allowed to recover. Of these, 4 pigs experienced sudden cardiac death at 14–17 days after ameroid implantation with microinfarcts of the left ventricular (LV) free wall, or anterlateral papillary muscle at autopsy. Additionally, 2 pigs were euthanized for joint effesions at 8 and 12 days post-ameroid implantation. Group I (ischemic controls, n=5) had no further intervention. Group II (TMR, n=4) underwent TMR in the area at risk at 6 weeks post-ameroid implantation. Group III (TMR-βgal), n=5) underwent TMR at 6 weeks with 3 equidistant intramyocardial injection of 100 μg of an expression plasmid encoding the gene for β-galactosidase (pSV-βgal) surrounding each TMR site. Group IV (VEGF, n=4) had sets of 3 epuidastant injections of 100 μg of an expression plasmid encoding the gene for VEGF-1, (pSV-VEGF) without TMR at 6 weeks. Group V (TMR-VEGF, n=5) had TMR with each site surrounded by 3 injections of 100 μg of pSV-VEGF at 6 weeks. All animals were harvested at 12 weeks after ameroid placement. Six additional pigs underwent TMR with either pSV-βgal or pSV-VEGF injections at 6 weeks, but were harvested at 8 weeks after ameroid placement. Group VI (n=5) were age and weight-matched normal Yorkshire pigs (45 kg) for comparison with groups I–V at 12 weeks.

Left mini-thoracotomy, ameroid implantation. Yorkshire pigs were premedicated with ketamine (10 mg/kg), intubated and maintained with general inhalational anaesthesia with 2% isoflorane. Cefazolin (40 mg/kg), MgSO4 (40 mg/kg), and bretylium tosylate (10 mg/kg) were given intravenously as prophylaxis against wound infection, and atrial and ventricular dysrythmias. Utilizing sterile operative technique, a left anterior mini-thoracotomy was performed through the fourth interspace and the pericardium incised and suspended to reveal the free wall of the left ventricle, atrioventricular groove, and left circumflex artery. A 2.5 mm ameroid constrictor (Research Instruments and Manufacturing, Corvallis, Oreg.) was placed around the proximal left circumflex artery.

Transesophageal echocardiogram. A transesophageal ultrasonic probe was placed to visualize left ventricular wall motion and to confirm placement of transmural channels by the $CO_2$ laser. A transesophageal ultrasonic probe was also placed to visualize LV wall motion pre- and post-ameroid with rapid atrial pacing (Medtronic 5375 Demand Pulse Generator) to ensure adequate positioning of the ameroid and to document baseline LV function with and without stress/rapid atrial pacing (Zlotnick et al., Surg. Forum 47:286–287, 1996). The pericardium was approximated and chest wall was closed in anatomic layers. An ipsilateral transient 28-Fr tube thoracostomy placed to suction was removed upon extubation, following which animals were allowed to recover 6 weeks to permit occlusion of the ameroid constrictor, with development of stable collateralization.

Transmyocardial Laser Revascularization. At 6 weeks post-ameroid implantation, animals underwent a repeat left mini-thoracotomy. A TEE probe was placed and the ventricle rapidly-paced to identify areas at risk along the left-ventricular free-wall. Images were digitally recorded for subsequent analysis by a cardiologist in a blinded fashion. An 800 watt CO2 laser (Heart laser, PLC Systems, Franklin, Mass.) was employed to produce transmural channels discharging 16 joules over a pulse width of 20 ms (Leung et al., Science 246:1306–1309, 1989). The channel density was approximately 1 channel/ $cm^2$ on the LV free wall, with care taken to avoid the coronary vasculature. Channels were confirmed by TEE, and by pulsatile flow during systole. 15–18 TMR areas per heart were marked by a 5-0 polypropylene stitch.

Gene delivery in ischemic myocardium. "Naked" double-stranded DNA in the form of an expression plasmid (pSV) containing the gene encoding VEGF-1 (Psv-VEGF-1), or a promoter-matched reporter gene construct, β-galactosidase (pSV,-gal), each employing an SV40 early promoter and enhancer region, was used to transfect ischemic myocardium. The biological activity of VEGF-1 secreted from smooth muscle cells transfected in vitro with this plasmid construct was confirmed by the promotion of endothelial cell proliferation in culture media derived from those pSV-VEGF-1 transfected cells.

Three equidistant 100 μl intramyocardial injections were placed with a 25-gauge needle within 4 mm of TMR sites. Identical doses of DNA (100 μg) each were used for myocardial transfection with either plasmid. Similar injections were placed in sites of non-TMR myocardium for the appropriate groups. A PGL2 expression plasmid, employing an SV40 early promoter and enhancer, but encoding the gene for firefly luciferase was injected at TMR sites in an identical manner to be used as a control in all animals to quantify target gene delivery and expression. Injection sites were marked by a 5-0 polypropylene stitch.

Median sternotomy. Animals were sacrificed via median sternotomy at six weeks post-transduction and post-TMR, or a total of 12 weeks post-ameroid implantation. Pre-anesthetic technique was as noted previously. With continuous ECG monitoring, access to the left femoral vein and artery, and left jugular vein and common carotid artery was obtained. TEE and epicardial echocardiography was performed in the paced and un-paced myocardium and images were recorded and stored for analysis as noted previously. Hearts were assessed for evidence of regional wall-motion abnormalities, and overall ventricular function in comparison with ischemic controls and age and weight-matched normal pigs. After systemic heparinization (100 units/kg), hearts were cold crystalloid cardioplegic arrested, and then removed from the mediastinum. These hearts were then flushed antegrade with microfil polymer (Flo-tek, Inc.) To outline the coronary circulation and provided resolution of the epicardial and sub-endocardial vessels, and preserved in formalin for histologic evaluation.

Results

Transgene expression. Myocardial trausgene expression was detected in 56 of 60 TMR-transfected sites 3 days after transfection (93%/), but in only 10 of 20 (50%/) non-TMR sites at the same time point (p less that 0.01 by two-tailed Fisher's Exact Test). The level of transgene expression did not vary among delivery methods for TMR-transfected sites at the doses tested. HVJ-liposomes yielded 992±146 pg β-gal/mg protein at doses of 5 μg/100 μl, and 1121±238 pg β-gal/mg protein at 15 μg/100 μl. Similarly, naked plasmid yielded 1099±322 pg β-gal/mg protein at doses of 100 μg/100 μl, and 761±179 pg β-gal/mg protein at dosed of 200 μg/100 μl.

However, the level of β-gal expressed in those sites reporting transgene expression in TMR-transfected sites (987±114 pg/mg) was approximately 2.4 times higher than in non-TMR transfected sites with positive expression (408±78 pg/mg; p less than 0.05 by two-tailed Student's t-test.

Functional analysis. Left ventricular free wall motion in the area at risk was assessed by a cardiologist in a blinded fashion. Hearts were scored as normal (no regional wall motion abnormality, normal systolic) or abnormal (hypokinetic, dyskinetic, or akinetic wall motion, or impaired systolic function). There were no wall motion abnormalities either prior to, or immediately following ameroid placement. At harvest, all of the ameroid alone hearts had impaired wall motion (0/5 normal), whereas 75% (¾) of the TMR, 60 % (3.5) of the TMR-βgal hearts, and 50% (²⁄₄) of the VEGF hearts displayed evidence of persistent wall motion abnormalities. Those hearts with impaired junction were generally hypokinetic in the area at risk, with occasional areas of akinesia There were discrete focal abnormalities in one of the TMR-treated hearts and one of the VEGF-treated hearts, both of which were scored as having normal overall wall motion. In contrast, all (⁵⁄₅) of the hearts treated with TMR-VEGF displayed no evidence of regional wall motion abnormality. Only the TMR-VEGF hearts had a statistically significantly different rate of wall motion abnormality compared with untreated ischemic hearts (=0.004 by two-tailed Fisher's Exact Test).

In addition, measures of cardiac function also demonstrated improved function in TMR/VEGF hearts as compared to TMR hearts. The load-dependent parameters, end diastolic elastance, its ratio with completely unloaded ventricular volume (theoretical), and recruitable stroke work, all indicated an increase in contractility in the TMR/VGF hearts. These results were supported by the TMR/VEGF load dependent factors, ejection fraction, end diastolic volume, and the derivative pressure versus time, which all indicated increased contractility in comparison to the TMR hearts.

Discussion

Photothermal effects of $CO_2$ laser. The chromophore for the energy discharged from a CO2 laser is water (Thomsen, Photochemistry 53:825–835, 1991). In high water content tissues such as myocardium, water-dominated tissue vaporization processes characteristic of infrared lasers dictate that three discrete zones exist in the perimeter surrounding a TMR channel (Thomsen, supra). The architecture of the injury has been characterized as having photochemical, photomechanical, and photothermal injury zones. The photochemical and photomechanical zones result in cell vaporization and cell coagulative necrosis, respectively. However, the photothermal zone is characterized by cellular injury with thermal temperature gradients between 40–100° C. (Thomsen, supra). Many cells in this zone do survive, and given our discovery that these cells exhibit enhanced gene expression, TMR and gene therapy are not only compatible, but synergistic.

Current applications for gene therapy. Because the "naked" plasmid is in injected locally in our studies, a greater spatial restriction upon plasmid-mediated transgene expression diminishes the possibility of significant uncontrolled regional or systemic exposure (Lin et al., Circ. 82:2217–2221, 1990). Furthermore, plasmid-mediated gene therapy may allow a single infection of a gene encoding for a proangiogenic agent to produce sustained local protein production after which it could act in paracrine fashion and obviate the need for repeated administration of protein (Mirhoseini et al., Lasers Surg. Med. 6: 459–61, 1986). The administration of this plasmid encoding VEGF during application of TMR may have additional synergistic benefits as well. The local injury induced by $CO_2$ laser TMR may result in increased expression of other factors necessary for successful collateral development, such as the flk/1/KDR receptor on endothelial cells. Such an effect would compliment the administration of VEGF plasmid and would not be achieved by simple injection of either the plasmid or protein.

Apparatus

The invention features an apparatus that includes a means for creating a channel in target tissue and a means for ejecting a molecule, such as a biologically active compound, out of the device into the target tissue. Biologically active compounds that can be injected into tissues using the device and method of the invention include nucleic acid molecules and proteins, such as those listed above. Although generally in solution, a biologically active compound administered using the apparatus or method of the invention can also be a superfine particulate, crystal, or powder that forms an emulsion or suspension. The pharmaceutical carrier can be a liquid or a gas. The molecule is preferably in an aqueous, isotonic sterile solution, e.g., a saline solution at about physiological pH.

A channel can be created in tissue by directing heat at the target tissue. In FIG. 1, portable heat-directing means 10 is connected by conduit 15 to a heat source (not shown), such as a laser source, an ultrasound source, or an electrical outlet. Heat directing means 10 has an aperture 11, through which heat is directed externally towards the target tissue. Where the heat source is a laser, laser path 12 extends from aperture 11. In other embodiments, sources of directable heat include an ultrasound probe and a thermal probe. In these embodiments, laser path 12 corresponds to the path along which a probe travels. The device can further include a means for projecting and retracting an ultrasound probe or a thermal probe to deliver and direct heat to the target tissue.

Turning to the injecting means, a molecule can be injected through a cannula. In FIG. 1, cannula 20 fluidly and sealably communicates with fluid chamber 30. Cannula 20 can have one opening at the end distal to fluid chamber 30, as shown in FIG. 1. A preferred cannula is a 25 gauge needle for adult heart tissue. Cannula 20 can also have a plurality of openings along the distal portion of the cannula to facilitate distribution of fluid 35 (plurality of openings not shown). In FIG. 1, fluid-ejecting means 40 is adjacent fluid chamber 30. Cannula projecting means 50 is adapted to project and to retract cannula 20. In FIG. 1, the cannula projecting means 50 is shown adjacent to fluid-ejecting means 40. However, cannula projecting means 50 can be placed in any convenient manner, including adjacent fluid chamber 30 or cannula 20.

Fluid chamber 30 can be filled through optional input valve 38 from a reservoir. Alternatively, fluid chamber 30 can be adapted to contain a compressible single-dose cartridge of a molecule to be injected into the target tissue, a cartridge containing multiple single-dosages, or a cartridge containing a reservoir sufficient for multiple dosages. Individual dosages can contain the same solution, solutions of different concentrations, or solutions having different solutes.

Connecting means 25 (FIG. 1) connects the means for creating a channel and the means for injecting a molecule. Connecting means 25 can include a casing that contains both assemblies, or a clamp or bracket that mounts one assembly on the other, with an adjustable sliding track. Connecting means 25 can also include a radial adjusting means 18 for adjusting the distance A. The distance A between laser path 12 and cannula 20 is preferably between 1 mm and 4 mm. Where laser path 12 and cannula 20 are approximately parallel, distance A is measured perpendicularly between laser path 12 and cannula 20. If laser path 12 and cannula 20 are not parallel, then distance A is measured in the plane of cannula 20, laser path 12, and the target. Radial adjusting means 18 can be adapted to adjust the relative position of either aperture 11 or cannula 20, or both. Radial adjusting means 18 can therefore be located adjacent one of aperture 11 and cannula 20, or between both of them.

Figure 2A:
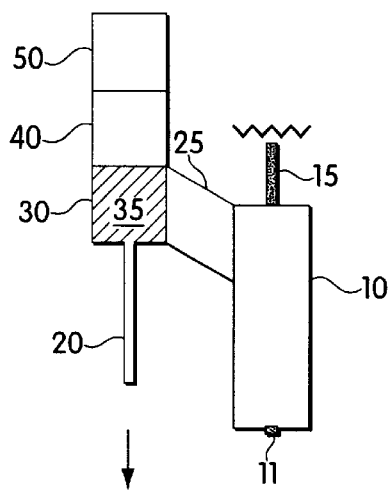
FIGS. 2A–2C are schematic representations of an embodiment of the apparatus of the invention, in which the means for injecting the biologically active compound is projected by a projecting means.

In operation, the means for applying heat and the means for injecting a molecule operate independently to accommodate any desired algorithm of channel creation and molecule delivery. In a preferred embodiment, cannula 20 is projected by projecting means 50 (FIG. 2A).

Figure 2B:
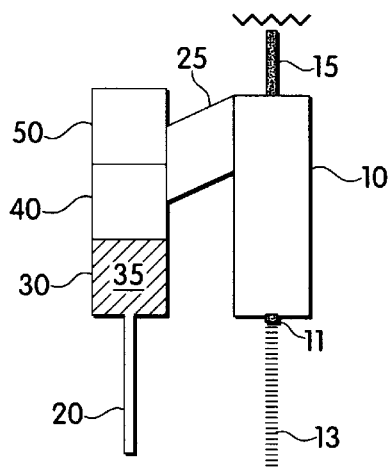
Figure 2C:
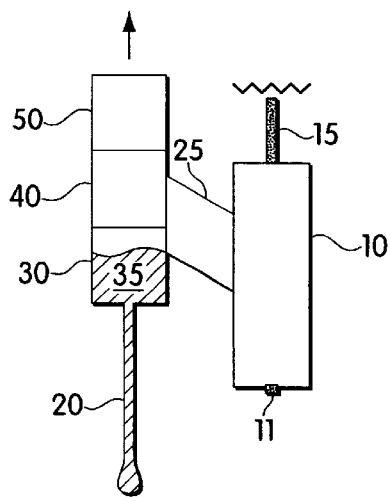

Simultaneously, heat is directed out of aperture 11, for example, in the form of a laser beam 13 (FIG. 2B). Laser beam 13 is terminated. As cannula 20 is retracted by projecting means 50, fluid 35 is propelled by fluid ejecting means 40 (FIG. 2C) along the track of the injection. Fluid 35 passes from fluid chamber 30 through cannula 20 to the one or more openings in the distal end of cannula 20.

In other methods of using the disclosed device, the order in which the cannula is injected into the tissue and the heat applied to create the channel are varied. For example, the heat can be directed out of aperture 11, terminated, and then the cannula 20 projected by a projecting means 50. Alternatively, the cannula 20 can be projected by a projecting means 50 and removed from the tissue before the heat is directed out of aperture 11. Also, the heat can be directed out of aperture 11, the cannula 20 projected into the tissue by a projecting means 50, and then the application of heat terminated.

Where an embodiment containing an ultrasound probe or a thermal probe is used, application of a laser beam is replaced with projecting the probe and termination of the laser beam is replaced with retracting the probe.

Figure 3A:
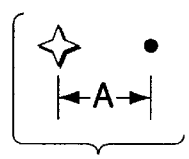
FIGS. 3A–3D are schematic representations of various arrangements of channel-creating means and cannulae in an apparatus of the invention.
Figure 3B:
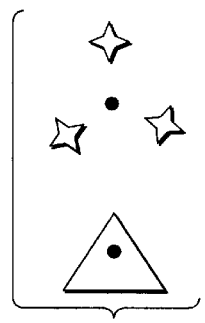
Figure 3C:
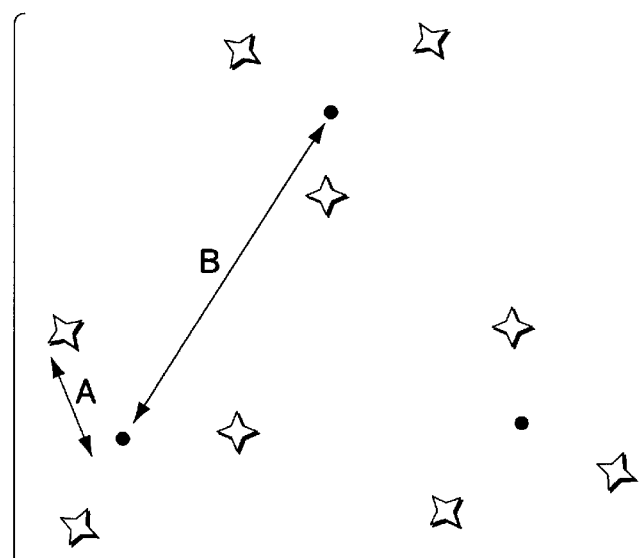
Figure 3D:
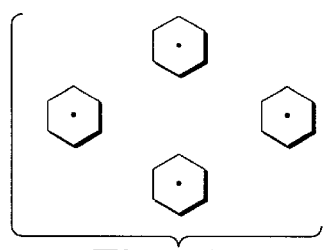

FIGS. 3A–3D show various channel (solid dot) and fluid (four-pointed star) patterns produced by combinations of one or more means for creating a channel and one or more means for injecting a molecule. The device of FIG. 2 would produce the channel and fluid pattern shown in FIG. 3A. Other arrangements include a device with one channel-creating means and three cannulae (FIG. 3B). The pattern can be schematically represented by a dot in a triangle. The pattern of FIG. 3C can be produced by operating the device of FIG. 3B three times, or by a device with three channel-creating means and nine cannulae. In either case, the channel-creating means were separated by a distance B. Similarly, the pattern of FIG. 3D can be created by a device with one channel-creating means and six cannulae.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method of enhancing injury-induced revascularization of a tissue as treatment of a disease, said method comprising the steps of:
   i) creating a track to tissue injury in said tissue, and
   ii) injecting into said tissue a revascularization-promoting molecule or a nucleic acid molecule encoding a revascularization-promoting molecule, wherein the track of the injection is in a predetermined direction relative to but not within, said tack of tissue injury,
   said method resulting in improvement of a condition of said disease to a greater degree than results from injury-induced revascularization treatment alone.

2. The method of claim 1, wherein said track of tissue injury is made with a laser.

3. The method of claim 2, wherein said laser is a carbon dioxide laser.

4. The method of claim 1, wherein time between creating said track of tissue injury and making said injection is less than 5.0 seconds.

5. The method of claim 4, wherein said time is less than 1.0 second.

6. The method of claim 4, wherein said time is less than 0.1 second.

7. The method of claim 1, wherein said revascularization-promoting molecule is a pro-angiogenic factor.

8. The method of claim 7, wherein said pro-angiogenic factor is vascular endothelial growth factor, fibroblast growth factor, platelet derived growth factor, insulin-like growth factor, epidermal growth factor, transforming growth factor, hepatocyte growth factor, proliferin, angiotropin, or angiopoietin.

9. The method of claim 1, wherein said nucleic acid molecule is naked DNA.

10. The method of claim 1, wherein cellular entry of said nucleic acid molecule is facilitated by non-live viral mediated transfer.

11. The method of claim 1, wherein said nucleic acid molecule is mixed with a lipid polyamine admixture.

12. The method of claim 1, wherein said nucleic acid molecule is operably linked to a promoter in a recombinant viral vector.

13. The method of claim 12, wherein said viral vector is a retrovirus, adenovirus, adeno-associated virus, or lentivirus.

14. The method of claim 1, wherein said tissue is muscle.

15. The method of claim 14, wherein said muscle is cardiac muscle.

16. The method of claim 1, wherein said condition improves as a result of increased vascularization of tissue affected by said disease.

17. The method of claim 1, wherein said disease is coronary artery disease.

18. The method of claim 1, wherein said condition of said disease is abnormal left ventricular wall motion or abnormal myocardial function.

19. The method of claim 1, wherein the number of said injections is equal IQ or greater than the number of said tracks of tissue injury in the treated tissue.

20. The method of claim 1, wherein said injection track is less than 4 mm from said track of tissue injury.

21. The method of claim 1, wherein said molecule undergoes sustained release.

22. A method of increasing expression of a gene in a tissue, said method comprising the steps of;
   i) creating a track tissue injury in said tissue, and
   ii) injecting into said tissue a nucleic acid molecule comprising said gene, wherein the track of the injection is in a predetermined direction relative to buy within said track of tissue injury,
   said method resulting in increased expression of said gene compared to expression that results firm injection of said nucleic acid molecule alone.

23. The method of claim 22, when the track of said injection parallels said of tissue injury.

24. The method of claim 22, said nucleic acid molecule is naked DNA.

25. The method of claim 22, wherein cellular entry of said nucleic acid molecule is facilitated by non-live viral mediated transfer.

26. The method of claim 22, wherein said nucleic acid molecule is mixed with a lipid polyamine admixture.

27. The method of claim 22, wherein said nucleic acid molecule is operably linked to a promoter in a recombinant viral vector.

28. The method of claim 22, wherein said viral vector is a retrovirus, adenovirus, adeno-associated virus, or lentivirus.

* * * * *